(12) United States Patent
Saitou et al.

(10) Patent No.: US 9,592,162 B2
(45) Date of Patent: Mar. 14, 2017

(54) APPARATUS FOR MANUFACTURING STRETCHABLE SHEET

(75) Inventors: Kazuma Saitou, Ichikai-machi (JP);
Akio Morita, Ichikai-machi (JP);
Takuo Yanashima, Utsunomiya (JP);
Shinnosuke Morita, Shanghai (JP)

(73) Assignee: KAO CORPORATION, Tokyo (JP)

( * ) Notice: Subject to any disclaimer, the term of this patent is extended or adjusted under 35 U.S.C. 154(b) by 928 days.

(21) Appl. No.: 13/990,347

(22) PCT Filed: Nov. 22, 2011

(86) PCT No.: PCT/JP2011/076931
§ 371 (c)(1),
(2), (4) Date: Jun. 28, 2013

(87) PCT Pub. No.: WO2012/073762
PCT Pub. Date: Jun. 7, 2012

(65) Prior Publication Data
US 2013/0264006 A1    Oct. 10, 2013

(30) Foreign Application Priority Data
Nov. 30, 2010    (JP) .................................. 2010-266044

(51) Int. Cl.
*A61F 13/15*    (2006.01)
(52) U.S. Cl.
CPC .. *A61F 13/15577* (2013.01); *A61F 13/15601* (2013.01); *A61F 13/15609* (2013.01)
(58) Field of Classification Search
None
See application file for complete search history.

(56) References Cited

U.S. PATENT DOCUMENTS

| | | |
|---|---|---|
| 4,776,911 A | 10/1988 | Uda et al. |
| 4,908,089 A | 3/1990 | Uda et al. |
| 2010/0075103 A1 | 3/2010 | Miyamoto |

FOREIGN PATENT DOCUMENTS

| | | |
|---|---|---|
| CN | 1198922 A | 11/1998 |
| CN | 101557929 A | 10/2009 |

(Continued)

OTHER PUBLICATIONS

International Search Report for PCT/JP2011/076931 dated Feb. 7, 2012.

(Continued)

*Primary Examiner* — Barbara J Musser
(74) *Attorney, Agent, or Firm* — Birch, Stewart, Kolasch & Birch, LLP (57) ABSTRACT

An apparatus (11) for producing stretchable sheet of the present invention includes a pair of conveyance belts (12, 13) which is separately arranged, elastic body winding means (14) which winds a threadlike elastic body (7) around the pair of conveyance belts (12, 13) and orients the threadlike elastic body (7) to a direction intersecting with a conveyance direction of continuous-length sheets, and integrating means which fixes the threadlike elastic body (7) to the continuous-length sheets. The conveyance belts (12, 13) include upper belts (12a, 13a) and lower belts (12b, 13b). Proceeding portions (12a', 13a') which convey the threadlike elastic body (7) at respective upper belts are inclined so that an upper side is located closer than a lower side to a center position (PC) between the conveyance belts, and proceeding portions (12b', 13b') which convey the threadlike elastic body (7) at respective lower belts are inclined so that a lower side is located closer than an upper side to a center position (PC).

11 Claims, 4 Drawing Sheets

(56) References Cited

FOREIGN PATENT DOCUMENTS

| | | |
|---|---|---|
| EP | 0876810 B1 | 3/2003 |
| JP | 63-243309 A | 10/1988 |
| JP | 2010-22549 A | 2/2010 |
| JP | 2011-127240 A | 6/2011 |

OTHER PUBLICATIONS

Extended European Search Report dated Apr. 23, 2014 for European Application No. 11845076.6.
International Preliminary Report on Patentability, and Translation of Written Opinion of the International Searching Authority, dated Jun. 13, 2013, for International Application No. PCT/JP2011/076931 (Forms PCT/IB/338, PCT/IB/373 and PCT/ISA/237).

APPARATUS FOR MANUFACTURING STRETCHABLE SHEET

TECHNICAL FIELD

The present invention relates to an apparatus for producing a stretchable sheet.

BACKGROUND ART

From viewpoints of being eco-friendly and reducing cost while suppressing materials and waste to the extent possible, there has been known an open-style disposable diaper which is produced by attaching a waist panel material to a rectangular absorbent body including an absorbent member after previously producing the waist panel material having a fastening tape in a separate process. From a viewpoint of fit, it is preferable that the waist panel material is a stretchable member. Generally, the waist panel material is formed by utilizing a stretchable film. However, since a stretchable film is expensive, it is preferable to form the waist panel material by using a so-called thread rubber which is a general member. Here, in a case where a process to obtain a waist panel material using thread rubber and a process to obtain an open-style disposable diaper by attaching the waist panel material to the absorbent body are continuously performed in sequence, a stretchable direction of the waist panel material formed by using the thread rubber generally becomes the same direction as the conveyance direction of the absorbent body, which is a direction perpendicular to a stretchable direction of the waist panel material required while wearing an open-style disposable diaper. Accordingly, in a case of producing an open-style disposable diaper by attaching the waist panel material formed by using thread rubber to the absorbent body in an inline process, the waist panel material formed by using thread rubber is required to be attached to the absorbent body after being rotated by 90°. Since an apparatus to rotate the waist panel material by 90° is required separately, equipment investment is increased.

As a method without using an apparatus to cause the rotation of 90° as described above, for example, Patent Literature 1 discloses a method for producing a stretchable sheet including a process of bonding a threadlike elastic body to a sheet in a state of being stretched while adhesive is applied to a permeable sheet moving in a length direction and the threadlike elastic body provided with tension is translated onto the adhesive applied face along the sheet face of the moving sheet toward the sheet moving direction in a zigzag state and a process of cutting the threadlike elastic body at both ends.

Further, Patent Literature 1 discloses an apparatus for producing a stretchable sheet which fixes a threadlike elastic body to a continuous-length sheet, by using a pair of conveyance belts which include two-tier belts to wind the threadlike elastic body respectively, after rearranging the threadlike elastic body wound around the pair of conveyance belts in a zigzag state in plane view to be parallel by setting a velocity difference between the upper belts and the lower belts.

However, since the two-tier belts in the apparatus using the two-tier belts disclosed in Patent Literature 1 are arranged in a two-tier fashion with a width direction of the both directed to a vertical direction, there is a risk that the threadlike elastic body cannot be stably fixed to a desired state owing to attrition at an upper side of the upper belt or a lower side of the lower belt, causing slipping and the like between the threadlike elastic body.

CITATION LIST

Patent Literature

Patent Literature 1: JP 63-243309 A

SUMMARY OF INVENTION

The present invention relates to providing a method for producing an absorbent article which can resolve drawbacks of the abovementioned conventional art.

Solution to Problem

An apparatus for producing a stretchable sheet according to the present invention includes a pair of conveyance belts which is separately arranged, elastic body winding means which winds a threadlike elastic body around the pair of conveyance belts and orients the threadlike elastic body in a direction intersecting with a conveyance direction of continuous-length sheets, and integrating means which fixes the threadlike elastic body to the continuous-length sheets. In addition, the pair of conveyance belts includes an upper belt and a lower belt respectively, each of the upper belt and the lower belt is an endless rotating belt including a proceeding portion which conveys the threadlike elastic body while contacting to the wound threadlike elastic body and a returning portion which moves in a direction opposite to the proceeding portion, the proceeding portion of the upper belt is inclined so that an upper side is located closer than a lower side to a center position between the conveyance belts, and the proceeding portion of the lower belt is inclined so that a lower side is located closer than an upper side to the center position between the conveyance belts.

In addition, the present invention is a method for producing a stretchable sheet which produces a stretchable sheet using the apparatus for producing stretchable sheet.

In addition, the present invention is a method for producing a disposable diaper which includes an absorbent body and right-left waist panels continuously arranged to both of right-left sides of the absorbent body in a longitudinal direction. The method includes producing a stretchable sheet with the apparatus for producing stretchable sheet, and producing the disposable diaper using the stretchable sheet as a forming material of the waist panels.

DESCRIPTION OF EMBODIMENTS

In the following, the present invention will be described based on preferable embodiments thereof with reference to the drawings.

Figure 1:
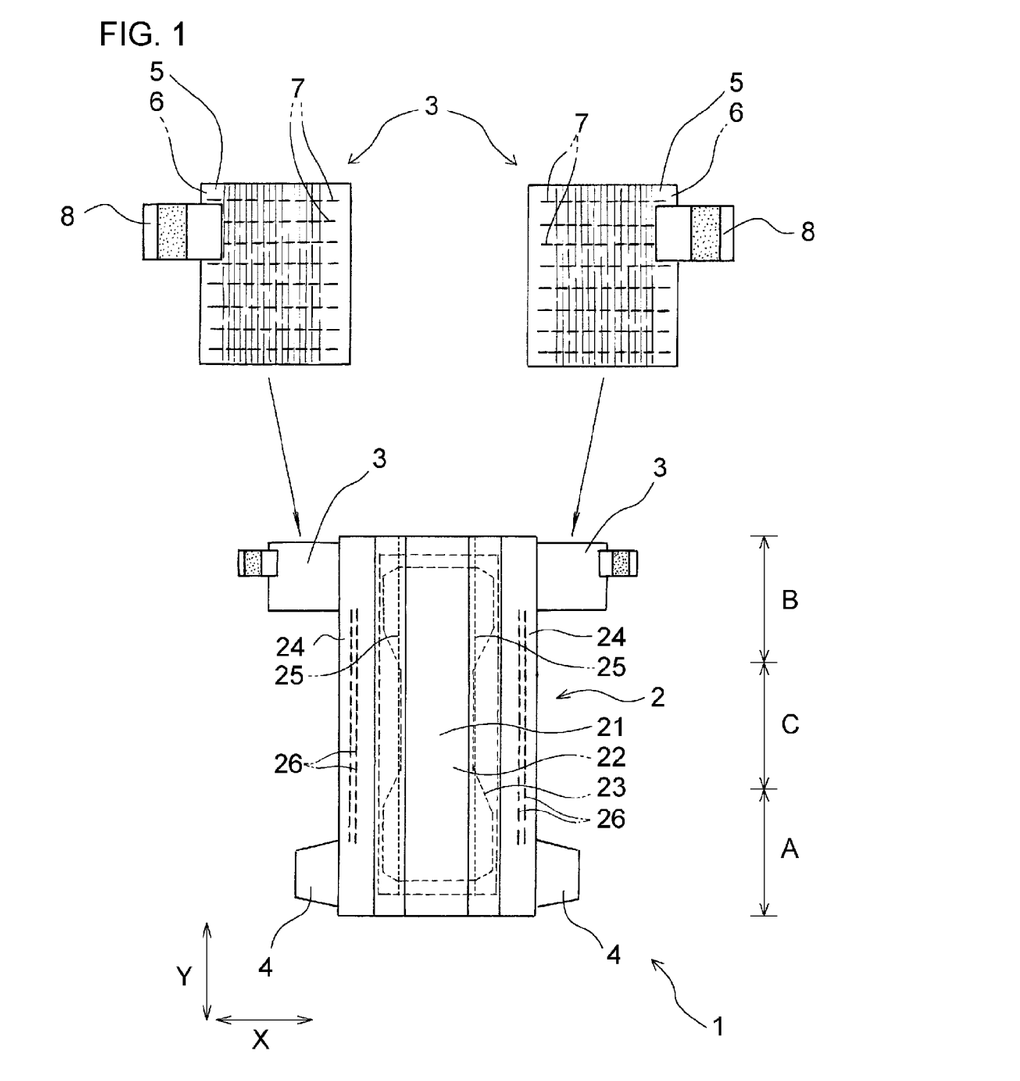
FIG. 1 is a plane view illustrating a waist panel material and an open-type disposable diaper using the waist panel material which are obtained in an embodiment of a method for producing a stretchable sheet and a method for producing a disposable diaper of the present invention.

A stretchable sheet produced in an embodiment of an apparatus for producing a stretchable sheet and a method for producing a stretchable sheet of the present invention is used as a waist panel 3 of an open-type disposable diaper 1, as illustrated in FIG. 1, for example. Accordingly, the open-type disposable diaper 1 in which a stretchable sheet produced in the present embodiment is used for a waist panel is firstly described. The disposable diaper 1 illustrated in FIG. 1 is also an example of a disposable diaper produced in the embodiment of the method for producing the disposable diaper of the present invention.

As illustrated in FIG. 1, the open-type disposable diaper 1 (hereinafter, also referred to as diaper 1) is provided with an absorbent body 2, which includes a front section A adapted to be worn about the front of a wearer, a rear section B adapted to be worn about the back of a wearer, and a crotch section C adapted to be worn between the front section A and the rear section B, and a right-left pair of waist panels 3, 3 continuously arranged at both outer sides of the rear section B. As illustrated in FIG. 1, the diaper 1 includes a right-left pair of panel materials 4, 4 continuously arranged at both outer sides of the front section A. Here, as illustrated in FIG. 1, the absorbent body 2 of the diaper 1 is rectangular in a state of being planarly-expanded. Further, as illustrated in FIG. 1, the panel material 4 of the diaper 1 is trapezoidal in a state of being planarly-expanded, and is fixed at the lower base side thereof having a larger length to the absorbent body 2 with means such as adhesive and fusion.

In the following description, the longitudinal direction of the absorbent body 2 (the longitudinal direction of the diaper 1 as well) is denoted by a Y-direction and the width direction of the absorbent body 2 (the width direction of the diaper 1 as well) is denoted by an X-direction.

The pair of waist panels 3, 3 is rectangular respectively in a state of being planarly-expanded. Each waist panel 3 includes two sheets 5, 6 and a plurality of threadlike elastic bodies 7 arranged between the two sheets 5, 6 in a stretched state. Each waist panel 3 is structured with a stretchable sheet which is fixed in a state that the threadlike elastic bodies 7 are stretched between the pair of sheets 5, 6 in a direction intersecting with the Y-direction. More specifically, as illustrated in FIG. 1, each waist panel 3 is formed by arranging threadlike elastic bodies between the two rectangular sheets 5, 6 having the same shape and size as being stretched in a direction (X-direction) intersecting with the Y-direction at approximately regular intervals in the Y-direction and integrally fixed to the threadlike elastic bodies with means such as adhesive and fusion. A fastening tape 8 is fixed to an outer end part in the X-direction of each rectangular waist panel 3 formed as described above with means such as adhesive and fusion. Further, each rectangular waist panel 3 is fixed at an inner end part in the X-direction to the rear section B of the absorbent body 2 with means such as adhesive and fusion and is continuously arranged outward in the X-direction from the rear section B. Here, although being stretched in a direction perpendicular to the Y-direction, the threadlike elastic bodies 7 provided to the waist panel 3 (stretchable sheet) produced in the present embodiment are only required to be stretched in a direction intersecting with the Y-direction.

The stretchable sheet structuring the waist panel 3 of the diaper 1 is fixed so that a conveyance direction y of the sheet at the time of production is in parallel to the Y-direction, and a direction x perpendicular to the conveyance direction of the sheet at the time of production corresponds to the X-direction.

As illustrated in FIG. 1, the absorbent body 2 includes a liquid permeable topsheet 21, a liquid impermeable or water-repellent backsheet 22, and a liquid-retaining absorbent member 23 which is interposed between both the sheets 21, 22. As illustrated in FIG. 1, the absorbent body 2 is fainted by joining the topsheet 21 which forms the inner face of the diaper 1 and the backsheet 22 which forms the outer face of the diaper 1 while interposing the absorbent member 23 between both the sheets 21, 22. Further, as illustrated in FIG. 1, the absorbent body 2 has standing gather forming sheets 24, 24 arranged along both side parts in the Y-direction. The standing gather forming sheets 24 are fixed to the topsheet 21 along the both side parts in the Y-direction of the absorbent body 2. Each standing gather forming sheet 24 includes an elastic member 25 for forming the standing gather along the vicinity of the side edge at the inner side in the X-direction. A section having a predetermined width from the side edges is separated from the topsheet 21 while the diaper is worn owing to a contraction force of the elastic member 25, so that the standing gather is formed. Further, elastic members 26 for forming leg gathers are arranged at sections arranged around legs at both side parts in the longitudinal direction of the absorbent body 2. Leg gathers are formed while the diaper is worn owing to contraction of the elastic members 26, so that excellent fitting is provided around legs.

Materials for forming the diaper 1 will be described.

Anything may be adopted without specific limitations as the sheets 5, 6 structuring the waist panels 3 and the panel materials 4 as long as being normally used respectively for an absorbent article such as a disposable diaper. For example, the sheets 5, 6 and the panel materials 4 may adopt non-woven, woven, film, a laminated sheet thereof, or the like. Anything may be adopted without specific limitations as the topsheet 21 and the backsheet 22 structuring the absorbent body 2 as long as being normally used respectively for an absorbent article such as a disposable diaper. For example, the topsheet 21 may adopt hydrophilic and liquid permeable non-woven or the like, and the backsheet 22 may adopt a liquid impermeable or water-repellent resin film, a laminated member of the resin film and nonwoven, or the like. The absorbent member 23 may adopt aggregate of fiber such as pulp fiber (or may be non-woven) or an absorbent core with particles of absorbent polymer held thereto covered with a core wrap sheet made of water permeable thin paper or non-woven, or the like. The standing gather forming sheet 24 structuring the standing gather may adopt a stretchable film, non-woven, woven, a laminated sheet thereof, or the like.

The threadlike elastic body 7 and the elastic member 25 structuring the standing gather may adopt threadlike stretchable materials formed of natural rubber, polyurethane, polystyrene-polyisoprene copolymer, polystyrene-polybutadiene copolymer, or polyethylene-α-olefin copolymer such as ethyl-acrylate-ethylene. The threadlike elastic body of the present invention may have a section being circular or square as well as being oval or narrow strip-shaped such as sectional rectangle, and may adopt a multifilament type. The width (or the diameter) of the threadlike elastic body is in the range of 0.1 to 0.3 mm, for example, and preferably equal to or less than 1 mm.

For example, the fastening tape 8 may be formed by sticking a hook member of a mechanical fastener on one face of a tape base material such as non-woven with thermal fusion, adhesive or the like.

Next, a preferable embodiment of the apparatus for producing a stretchable sheet of the present invention will be described with reference to FIGS. 2 to 4.

Figure 2:
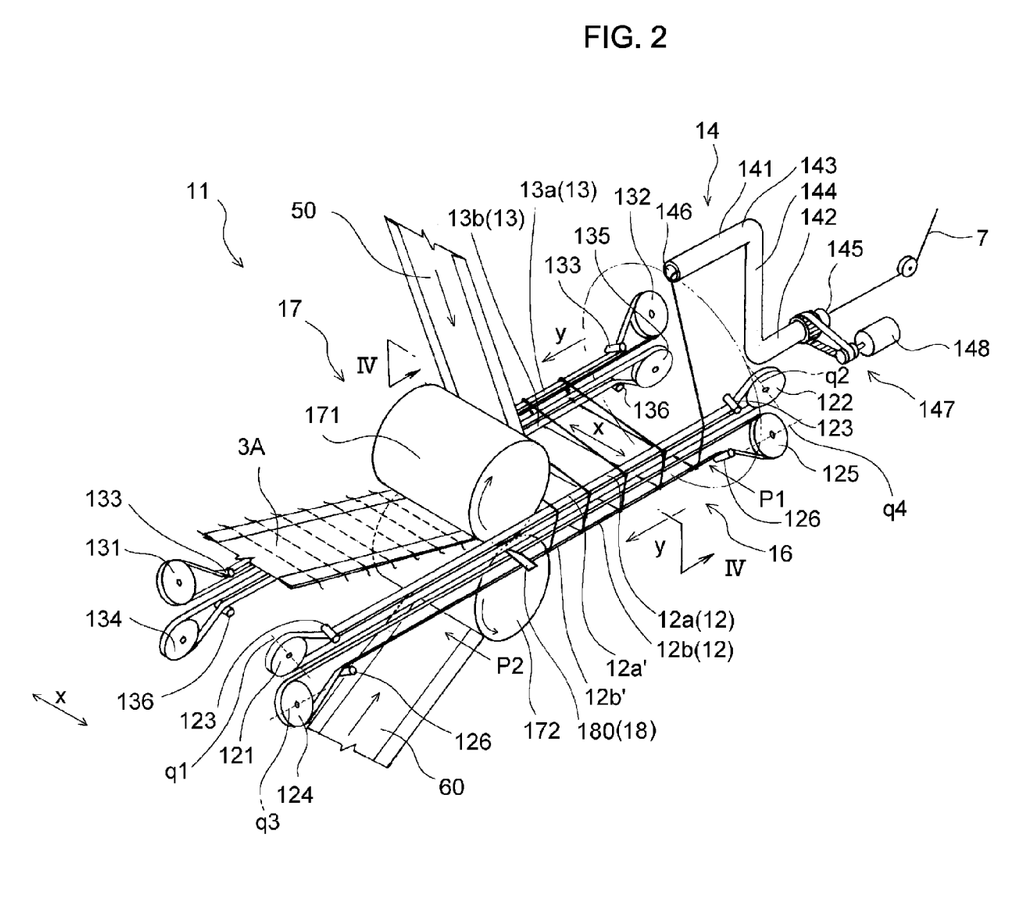
FIG. 2 is a schematic perspective view illustrating an embodiment of an apparatus for producing a stretchable sheet of the present invention.

As illustrated in FIG. 2, an apparatus 11 for producing a stretchable sheet (hereinafter, also referred as producing apparatus 11) is an apparatus for continuously producing a stretchable sheet 3A used for the waist panel 3, and is provided with conveyance means 16 which includes a pair of conveyance belts 12, 13 being separately arranged, a rotary arm 14 (elastic body winding means) which winds the threadlike elastic body 7 around the pair of conveyance belts 12, 13 and orients the threadlike elastic body 7 to a direction (a direction extending in the x-direction) intersecting with the conveyance direction (y-direction) of continuous-length sheets 50, 60, integrating means 17 which fixes the threadlike elastic body 7 to the continuous-length sheets 50, 60, and cutting means 18 which cuts the threadlike elastic body 7 extending from both end parts respectively in the width direction of the continuous-length sheets 50, 60.

The pair of conveyance belts 12, 13 is arranged to be separated in a direction (x-direction) perpendicular to the conveyance direction (y-direction) of the sheets 50, 60. The conveyance means 16 conveys the threadlike elastic body 7 between the pair of continuous-length sheets 50, 60 with the pair of conveyance belts 12, 13.

The integrating means 17 fixes the threadlike elastic body 7 in a stretched state between the pair of continuous-length sheets 50, 60 using a pair of nip rollers 171, 172.

Figure 3:
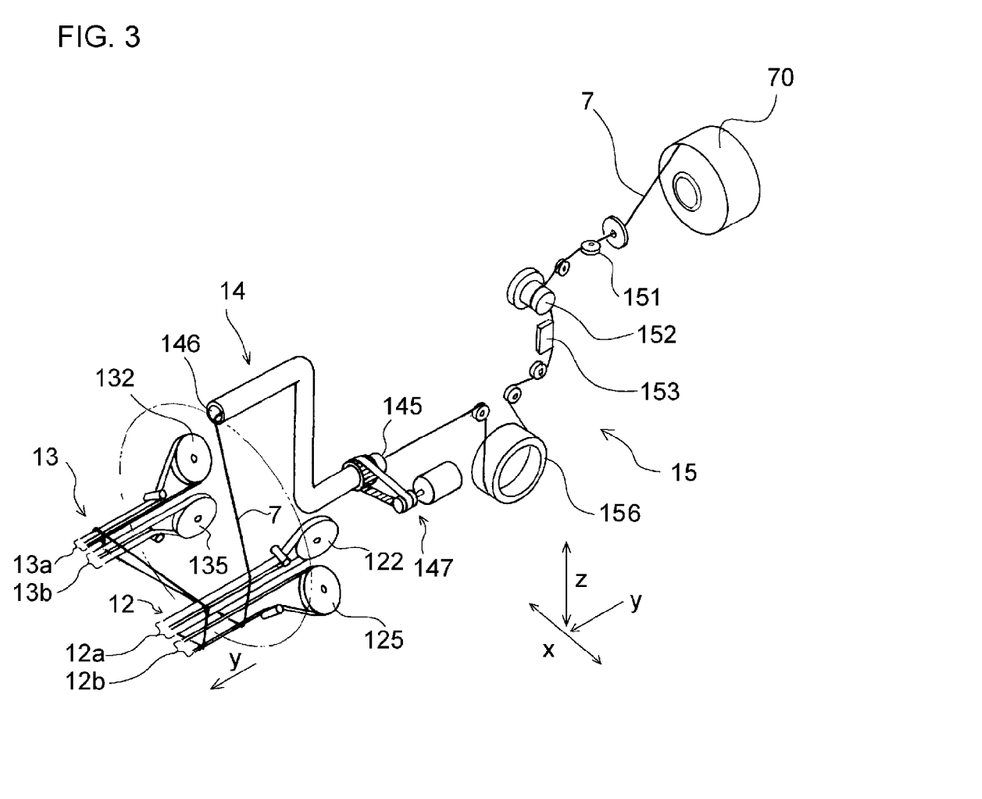
FIG. 3 is a perspective view illustrating a structure at an upstream side from a rotary arm (elastic body winding means) of the apparatus illustrated in FIG. 2.

As illustrated in FIG. 3, the apparatus 11 includes elastic body supplying means 15 which continuously unreels the threadlike elastic body 7 and introduces the threadlike elastic body 7 to the rotary arm 14 (elastic body winding means) in a stretched state.

The conveyance direction of the sheets corresponds to the conveyance direction of the threadlike elastic body 7 wound around the pair of conveyance belts 12, 13 or the conveyance direction of the sheet (belt-shape sheet 50 and/or 60) integrated with the threadlike elastic body 7.

The y-direction of an arrow in FIG. 2 is the conveyance direction of the sheet indicating the conveyance direction of the threadlike elastic body 7 or the pair of continuous-length sheets 50, 60. The y-direction is the same direction as the conveyance direction of the waist panel 3 (stretchable sheet) and the conveyance direction of continuous members of the diaper 1 to which the waist panel 3 (stretchable sheet) is attached finally produced in the present embodiment. Further, the x-direction of an arrow in FIG. 2 is the width direction of the continuous-length sheets 50, 60 being the direction perpendicular to the conveyance direction of the sheets. Further, a z-direction of an arrow in FIG. 2 is a direction in which the later-mentioned nip rollers 171, 172 in a pair face each other.

Figure 4:
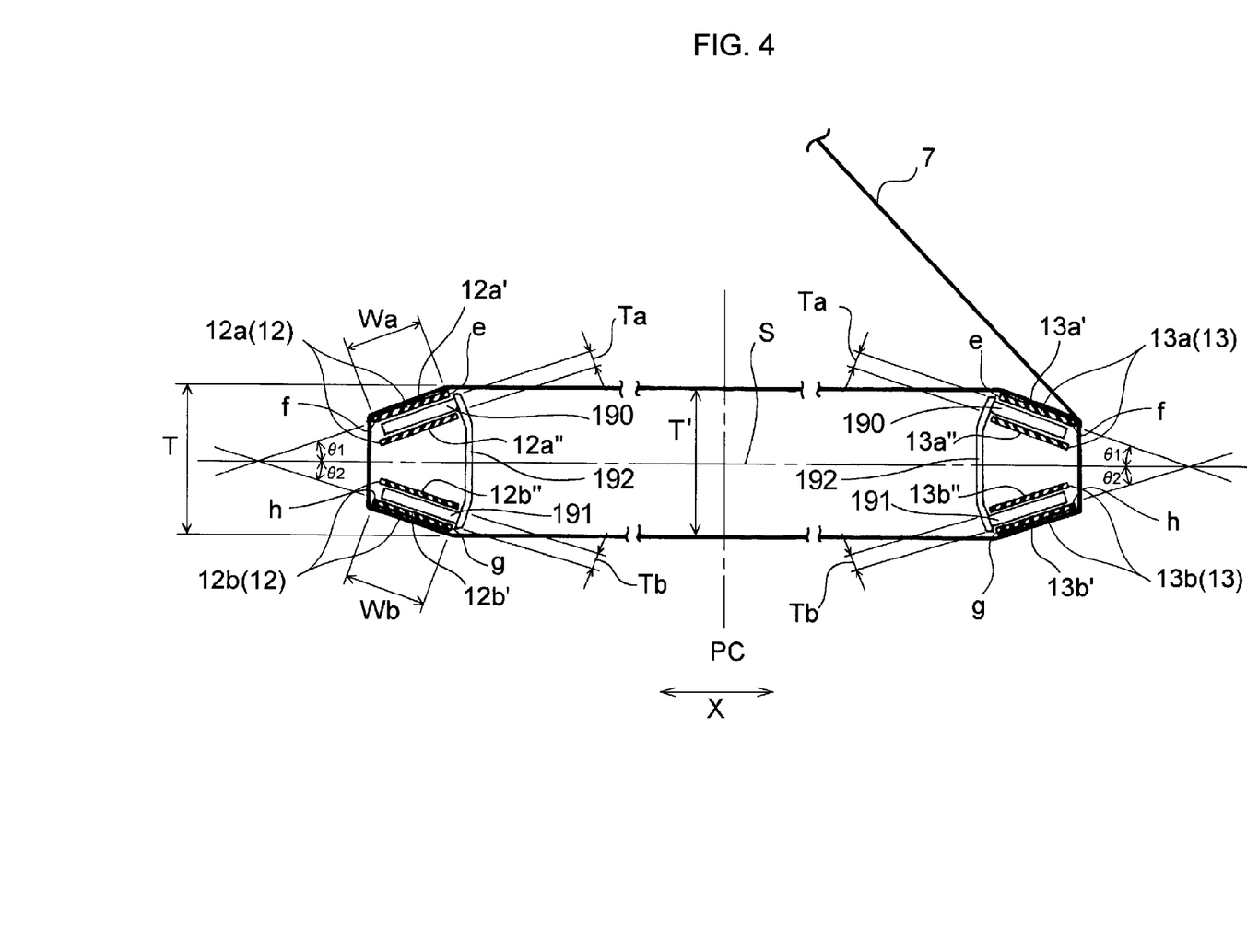
FIG. 4 is a sectional view of the device illustrated in FIG. 2 along a line IV-IV.

As illustrated in FIGS. 2 and 4, the conveyance belt 12 of the conveyance means 16 includes a two-tier belt having an upper belt 12a and a lower belt 12b. The upper belt 12a and the lower belt 12b are endless rotating belts, respectively.

As illustrated in FIG. 2, the upper belt 12a is routed between a pair of pulleys 121, 122. A rotation axis q1 of the pulley 121 and the rotation axis q2 of the pulley 122 are in parallel to each other and are inclined with respect to a straight line perpendicular to an elastic body conveyance face S (see FIG. 4), respectively. Here, the elastic body conveyance face S denotes a plane face connecting the pair of conveyance belts 12, 13 at a same height position (preferably a center position of the upper belt and the lower belt).

As illustrated in FIGS. 2 and 4, the upper belt 12a includes a proceeding portion 12a' which conveys the threadlike elastic body 7 in the y-direction by contacting the threadlike elastic body 7 wound by the rotary arm 14 (elastic body winding means) and a returning portion 12a" which moves in a direction opposite to the proceeding portion 12a'. The proceeding portion 12a' of the upper belt 12a is a portion moving from the pulley 122 to the pulley 121 in the upper belt 12a, and the returning portion 12a" is a portion moving from the pulley 121 to the pulley 122 in the upper belt 12a.

An outer face of the proceeding portion 12a' of the upper belt 12a is abutted to a pair of rollers 123. As illustrated in FIGS. 2 and 4, owing to the rollers 123 pressing the proceeding portion 12a' while rotating, a region where a distance Ta (see FIG. 4) between the proceeding portion 12a' and the returning portion 12a" is narrowed to be equal to or smaller than a diameter of the pulleys 121, 122 (preferably equal to or smaller than two thirds of the diameter, and more preferably equal to or smaller than a half) is formed between the pair of rollers 123.

The distance Ta (see FIG. 4) is preferably in a range of 3 to 25% of a height T of the conveyance belts 12, 13 and more preferably in a range of 5% to 15%. As illustrated in FIG. 4, the height T of the conveyance belts 12, 13 denotes a distance from an upper side e of the proceeding portion of the upper belt to a lower side g of the proceeding portion of the lower belt in a direction perpendicular to the elastic body conveyance face S for each of the conveyance belts 12, 13. Here, since the size of the height T is to be a reference of the conveyor from a viewpoint of facilitating arrangement of the threadlike elastic body between the nip rollers 171, 172 and space-saving, ratio to the height T is defined. The value of the height T is preferably equal to or smaller than 25% of the diameter of the nip rollers, and more preferably equal to or smaller than 20%. The diameter of the nip rollers is the diameter of the nip rollers 171, 172.

The ratio of the distance Ta (see FIG. 4) to the height T is preferable to be in the above numerical range for the following reason. When the ratio of the distance Ta to the height T, which is a reference, is too large, thickness of the belt is forced to be thin, so that the belt is likely to be worn.

As described above, in the producing apparatus 11 of the present embodiment, rotation axes q1, q2 of the pair of pulleys 121, 122 are inclined with respect to a straight line perpendicular to the elastic body conveyance face S, and rotation axes of the pair of rollers 123 are inclined approximately in parallel to the rotation axes q1, q2 of the pair of pulleys 121, 122 as well.

Accordingly, as illustrated in FIG. 4, the proceeding portion 12a' of the upper belt 12a is inclined so that the upper side e thereof is located closer than a lower side f thereof to a center position PC between the conveyance belts 12, 13. Further, the rotation axes q1, q2 of the pulleys 121, 122 are perpendicular to the inclined proceeding portion 12a' of the upper belt 12a.

From the abovementioned viewpoint of facilitating arrangement of the threadlike elastic body between the nip rollers 171, 172 and space-saving, an inclination angle θ1 (see FIG. 4) of the proceeding portion 12a' of the upper belt 12a with respect to the abovementioned elastic body conveying face S is preferably in a range of 1 to 45°, and more preferably in a range of 5 to 20° more preferably.

As illustrated in FIG. 2, the lower belt 12b is routed between the pair of pulleys 124, 125. A rotation axis q3 of the pulley 124 and the rotation axis q4 of the pulley 125 are in parallel to each other and are inclined with respect to a straight line perpendicular to the elastic body conveyance face S, respectively.

As illustrated in FIGS. 2 and 4, the lower belt 12b includes a proceeding portion 12b' which conveys the threadlike elastic body 7 in the y-direction by contacting to the threadlike elastic body 7 wound by the rotary arm 14 (elastic body winding means) and a returning portion 12b" which moves in an opposite direction to the proceeding portion 12b'. The proceeding portion 12b' of the lower belt 12b is a section moving from the pulley 125 to the pulley 124 in the lower belt 12b, and the returning portion 12b" is a section moving from the pulley 124 to the pulley 125 in the lower belt 12b.

An outer face of the proceeding portion 12b' of the upper belt 12b is abutted to the pair of rollers 126. As illustrated in FIGS. 2 and 4, owing to the rollers 126 pressing the proceeding portion 12b' while rotating, a region where a distance Tb (see FIG. 4) between the proceeding portion 12b' and the returning portion 12b" is narrowed to be equal to or smaller than a diameter of the pulleys 124, 125 (preferably equal to or smaller than two thirds of the diameter, and more preferably equal to or smaller than a half) is formed between the pair of rollers 126. Similarly to the distance Ta, the distance Tb (see FIG. 4) is preferably in a range of 3 to 25% of a height T, and more preferably in a range of 5 to 15%.

As described above, in the producing apparatus 11 of the present embodiment, rotation axes q3, q4 of the pair of pulleys 124, 125 are inclined with respect to a straight line perpendicular to the elastic body conveyance face S, and rotation axes of the pair of rollers 126 are inclined approximately in parallel to the rotation axes q3, q4 of the pair of pulleys 124, 125 as well.

Accordingly, as illustrated in FIG. 4, the proceeding portion 12b' of the lower belt 12b is inclined so that the lower side g thereof is located closer than lower side h thereof to a center position PC between the conveyance belts 12, 13. Further, the rotation axes q3, q4 of the pulleys 124, 125 are perpendicular to the inclined proceeding portion 12b' of the lower belt 12b.

An inclination angle θ2 (see FIG. 4) of the proceeding portion 12b' of the lower belt 12b with respect to the abovementioned elastic body conveyance face S is similar to the abovementioned preferable inclination angle of the proceeding portion 12a' of the upper belt 12a.

The conveyance belt 13 of the present embodiment has the same structure as that of the conveyance belt 12 except for being bilaterally symmetric with respect to the center position PC between the conveyance belts 12, 13. Accordingly, the conveyance belt 13 is similar to the conveyance belt 12 unless otherwise noted. Here, although the rotation axes of respective pulleys of the conveyance belt 13 are not illustrated, the same structure is also provided except for being bilaterally symmetric to the respective rotation axes q1 to q4 of the conveyance belt 12.

As illustrated in FIGS. 2 and 4, the conveyance belt 13 of the conveyance means 16 includes a two-tier belt of an upper belt 13a and a lower belt 13b. The upper belt 13a is an endless rotating belt, and is routed between pulleys 131, 132. The upper belt 13a includes a proceeding portion 13a' which conveys the threadlike elastic body 7 in the y-direction by contacting to the threadlike elastic body 7 and a returning portion 13a" which moves in a direction opposite to the proceeding portion 13a'.

An outer face of the proceeding portion 13a' of the upper belt 13a is abutted to the pair of rollers 133. Owing to the rollers 133 pressing the proceeding portion 13a' while rotating, a region where the distance Ta (see FIG. 4) between the proceeding portion 13a' and the returning portion 13a" is narrowed to be equal to or smaller than a diameter of the pulleys 131, 132 (preferably equal to or smaller than two thirds of the diameter, and more preferably equal to or smaller than a half) is formed between the pair of rollers 133. The preferable ratio of the distance Ta to the height T is similar to the upper belt of the conveyance belt 12.

In the producing apparatus 11 of the present embodiment, rotation axes of the pair of pulleys 131, 132 are inclined with respect to a straight line perpendicular to the elastic body conveyance face S, and rotation axes of the pair of rollers 133 are inclined as well as are approximately in parallel to the rotation axes of the pair of pulleys 131, 132.

Accordingly, similarly to the proceeding portion 12a' of the upper belt 12a, the proceeding portion 13a' of the upper belt 13a is inclined so that the upper side e thereof is located closer than the lower side f thereof to the center position PC between the conveyance belts 12, 13. Further, the rotation axes of the pulleys 131, 132 are perpendicular to the inclined proceeding portion 13a' of the upper belt 13a. The inclination angle θ1 (see FIG. 4) of the proceeding portion 13a' of the upper belt 13a with respect to the elastic body conveyance face S is similar to the abovementioned preferable inclination angle of the proceeding portion 12a' of the upper belt 12a of the conveyance belt 12.

The lower belt 13b is an endless rotating belt, and is routed between pulleys 134, 135. The lower belt 13b includes a proceeding portion 13b' which conveys the threadlike elastic body 7 in the y-direction and a returning portion 13b" which moves in a direction opposite to the proceeding portion 13b'.

An outer face of the proceeding portion 13b' of the lower belt 13b is abutted to the pair of rollers 136. Owing to that the rollers 136 press the proceeding portion 13b' while rotating, a region where the distance Tb (see FIG. 4) between the proceeding portion 13b' and the returning portion 13b" is narrowed to be equal to or smaller than a diameter of the pulleys 134, 135 (preferably equal to or smaller than two thirds of the diameter, and more preferably equal to or smaller than a half) is formed between the pair of rollers 136. The preferable ratio of the distance Tb to the height T is similar to the lower belt of the conveyance belt 12.

As described above, in the producing apparatus 11 of the present embodiment, rotation axes of the pair of pulleys 134, 135 are inclined with respect to a straight line perpendicular to the elastic body conveyance face S, and rotation axes of the pair of rollers 136 are inclined approximately in parallel to the rotation axes of the pair of pulleys 134, 135 as well.

Accordingly, similarly to the proceeding portion 12b' of the lower belt 12b, the proceeding portion 13b' of the lower belt 13b is inclined as having the lower side g thereof located closer than the upper side h thereof to the center position PC between the conveyance belts 12, 13. Further, the rotation axes of the pulleys 134, 135 are perpendicular to the inclined proceeding portion 13b' of the lower belt 13b, respectively.

The inclination angle θ2 (see FIG. 4) of the proceeding portion 13b' of the lower belt 13b with respect to the elastic body conveyance face S is similar to the abovementioned preferable inclination angle of the proceeding portion 12b' of the lower belt 12b of the conveyance belt 12.

The pulleys 121, 124, 131, 134 are located at the downstream side of the pair of nip rollers 171, 172 which fix the threadlike elastic body 7 in a stretched state between the pair of continuous-length sheets 50, 60 respectively, and the pulleys 122, 125, 132, 135 are located at the upstream side of the pair of nip rollers 171, 172 respectively. The pulleys 121, 124 are arranged approximately at same positions in the y-direction in an upper and lower two-tier fashion and the pulleys 122, 125 are arranged approximately at same positions in the y-direction in an upper and lower two-tier fashion as well. Further, the pulleys 123, 126 are arranged approximately at same positions in the y-direction in an upper and lower two-tier fashion as well. The pulleys 131, 134 are arranged approximately at same positions in the y-direction in an upper and lower two-tier fashion and the pulleys 132, 135 are arranged approximately at same positions in the y-direction in an upper and lower two-tier fashion as well. Further, the pulleys 133, 136 are arranged approximately at same positions in the y-direction in an upper and lower two-tier fashion as well.

The pulley 121 (pulley 124), the pulley 122 (pulley 125) and the roller 123 (roller 126) are located at the outer side in the x-direction from the outer end part of the continuous-length sheets 50, 60 in the x-direction, respectively. Further, the pulley 131 (pulley 134), the pulley 132 (pulley 135) and the roller 133 (roller 136) are located at the outer side in the x-direction from the outer end part of the continuous-length sheets 50, 60 in the x-direction.

A servomotor (not illustrated) is continuously arranged at a driving portion of the pulley 121 and the pulley 124 respectively, and is capable of varying a rotation speed of the upper belt 12a and the lower belt 12b respectively. A servomotor (not illustrated) is continuously arranged at a driving portion of the pulley 131 and the pulley 134 respectively and is capable of varying a rotation speed of the upper belt 13a and the lower belt 13b respectively. Each of the rollers 123, 126, 133, 136 rotates as following movement of the belts.

As illustrated in FIG. 2, the conveyance belt 12 (the upper belt 12a and the lower belt 12b) is arranged from the upstream side to the downstream side of the pair of nip rollers 171, 172 as being routed around the pulleys 121, 122 and the pulleys 124, 125 arranged as described above. Further, the conveyance belt 13 (the upper belt 13a and the lower belt 13b) is arranged from the upstream side to the downstream side of the pair of nip rollers 171, 172 as being routed around the pulleys 131, 132 and the pulleys 134, 135 arranged as described above. Further, the conveyance belt 12 (the upper belt 12a and the lower belt 12b) and the conveyance belt 13 (the upper belt 13a and the lower belt 13b) are located at the outer side of the continuous-length sheets 50, 60 in the x-direction and are arranged being bilaterally symmetric with each other.

The threadlike elastic body 7 wound around the conveyance belt 12 and the conveyance belt 13 is conveyed with the movement of the proceeding portions 12a', 12b', 13a', 13b' of each of the upper belt 12a and the lower belt 12b of the conveyance belt 12 and the upper belt 13a and the lower belt 13b of the conveyance belt 13. The respective moving speed is the respective feeding speed of the upper and lower belts 12a, 12b of the conveyance belt 12 and the upper and lower belts 13a, 13b of the conveyance belt 13.

Both of the conveyance belt 12 (the upper belt 12a and the lower belt 12b) and the conveyance belt 13 (the upper belt 13a and the lower belt 13b) are preferred to be timing belts. The rotation speed of the conveyance belt 12 (the upper belt 12a and the lower belt 12b) and the conveyance belt 13 (the upper belt 13a and the lower belt 13b), that is, the rotation speed of the servomotors (not illustrated) arranged at the respective driving portions of the pulley 121, the pulley 124, the pulley 131 and the pulley 134 is controlled by a controlling portion (not illustrated) provided to the producing apparatus 11.

As illustrated in FIG. 2, the rotary arm 14 is provided with an arm portion 141 including a shaft portion 142, an orbiting portion 143 and a connecting portion 144 and a driving mechanism 147 which rotates the arm portion 141 with the center line of the shaft portion 142 as a rotation axis. The connecting portion 144 is connected to the shaft portion 142 and the orbiting portion 143 as being angled thereto respectively, and the orbiting portion 143 and the shaft portion 142 is are approximately in parallel to each other. The shaft portion 142 has an inlet port 145 for the threadlike elastic body 7 at an end thereof and the orbiting portion 143 has an outlet port 146 for the threadlike elastic body 7 at an end thereof. The threadlike elastic body 7 introduced from the inlet port 145 is smoothly led out from the outlet port 146 passing through the shaft portion 142, the connecting portion 144 and the orbiting portion 143. It is also possible to arrange a variety of known members (a driven roll, a low-friction member or the like) which can reduce friction against the threadlike elastic body 7 at a bent part of the arm portion 141, the outlet port 146 and the like.

In the orbiting portion 143, the outlet port 146 is arranged at a position at the downstream side from an end part of the upstream side of the conveyance belt 12 (the upper belt 12a and the lower belt 12b) and the conveyance belt 13 (the upper belt 13a and the lower belt 13b). In the rotary arm 14, a servomotor 148 is attached to the drive portion (shaft portion 142). Rotation of the servomotor 148 causes the orbiting portion 143 to orbit on outer periphery of the conveyance belt 12 (the upper belt 12a and the lower belt 12b) and the conveyance belt 13 (the upper belt 13a and the lower belt 13b). A diameter of an orbit on which the outlet port 146 is rotated is larger than a distance between outer faces of the pair of conveyance belts 12, 13 (the maximum distance in bilateral direction in FIG. 4).

Owing to the rotary arm 14 described above, the introduced threadlike elastic body 7 can be continuously wound to the outer periphery sides at end parts of the upstream side of the conveyance belt 12 (the upper belt 12a and the lower belt 12b) and the conveyance belt 13 (the upper belt 13a and the lower belt 13b). A rotation speed of the rotary arm 14, that is, a rotation speed of the servomotor 148 is controlled by the control unit (not illustrated) provided to the producing apparatus 11.

As illustrated in FIG. 3, the elastic body supplying means 15 is provided with a tensor 151 which is located at the downstream side of the bobbin 70 to which the threadlike elastic body 7 is wound and which applies tension to the threadlike elastic body 7 with braking, a reel-out roller 152 which is located at the downstream side of the tensor 151 and which unreels the threadlike elastic body 7 from the bobbin 70, and a tension measuring unit 153 which measures the tension as being located at the downstream side of the reel-out roller 152. A rotation axis of the reel-out roller 152 is arranged in the x-direction. A servomotor (not illustrated) is attached to a drive portion of the reel-out roller 152. The reel-out roller 152 is used with the threadlike elastic body 7 wound to the outer circumference thereof in two turns. A control portion (not illustrated) provided to the producing apparatus 11 controls the rotation speed of the servomotor (not illustrated), that is, the rotation speed of the reel-out roller 152 based on the detection output from the tension measuring unit 153. Thus, the threadlike elastic body 7 having a predetermined tension can be unreeled from the bobbin 70.

As illustrated in FIG. 3, the elastic body supplying means 15 is provided with a feed roller 156 located at the downstream side of the reel-out roller 152. The feed roller 156 is arranged between the rotary arm 14 and the reel-out roller 152 with a rotation axis thereof arranged in the x-direction. In the feed roller 156, a servomotor (not illustrated) is attached to the drive portion. The rotation speed of the servomotor (not illustrated), that is, the rotation speed of the feed roller 156 is controlled by the control portion (not illustrated) provided to the producing apparatus 11.

As illustrated in FIGS. 2 and 4, the integrating means 17 includes the pair of nip rollers 171, 172. The pair of nip rollers 171, 172 may adopt cylindrical rollers made of metal or low hardness silicon-rubber. A servomotor (not illustrated) is attached to a drive portion for either of the pair of nip rollers 171, 172 and a rotation speed thereof is controlled by the control unit (not illustrated) provided to the producing apparatus 11. The pair of nip rollers 171, 172 is provided with a gear for drive transmission respectively at each rotation axis. The drive means (not illustrated) can control a rotation speed of the servomotor (not illustrated), that is, a rotation speed of one of the nip rollers 171, 172 based on a producing speed of stretchable sheets. At that time, owing to engagement of the gears for drive transmission, drive force is transmitted to the other of the nip rollers 171, 172 as well, so that the pair of nip rollers 171, 172 can be rotated. Bearing sections of the pair of nip rollers 171, 172 are pressurized respectively by utilizing force of hydraulic pressure, air pressure, a spring or the like for reliably fixing the stretched threadlike elastic body between the pair of continuous-length sheets 50, 60.

As illustrated in FIG. 2, the pair of nip rollers 171, 172 is located between the inner circumferential side of the conveyance belt 12 and the inner circumferential side of the conveyance belt 13.

Further, the integrating means 17 is provided with an adhesive coater (not illustrated) which applies adhesive to the continuous-length sheet 50 and/or 60 before converging with the threadlike elastic body 7. The adhesive coater applies adhesive in an arbitrary pattern to a face of the continuous-length sheet 50 faced to the continuous-length sheet 60 and/or a face of the continuous-length sheet 60 faced to the continuous-length sheet 50. The applying aspect of the adhesive may be pattern applying such as in stripes, spirals, sinewaves or the like, may be spraying to the entire face, or may be applying in a solid manner. By pressurizing the continuous-length sheet 50 and/or 60 in a state that the adhesive is applied thereto and the threadlike elastic body 7 is sandwiched therebetween, the threadlike elastic body 7 is reliably fixed between the continuous-length sheets 50, 60.

As illustrated in FIG. 2, the cutting means 18 includes cutters 180 respectively with a sharp cutting blade at a portion to which the conveyed threadlike elastic body 7 is abutted (the cutter 180 at the conveyance belt 13 side is not illustrated in the drawing). The cutter 180 is arranged at a position to be abutted to the threadlike elastic body 7 with a support body (not illustrated). The threadlike elastic body 7 is cut by being pressed to the cutter 180 after being conveyed by the conveyance belts 12, 13. The cutter 180 is located between the upper belt 12a and the lower belt 12b and between the upper belt 13a and the lower belt 13b. A position in the x-direction for cutting the threadlike elastic body 7 with the cutting means 18 may be between the nip rollers 171, 172 and the conveyance belts 12, 13. Further, a variety of known entity capable of cutting the threadlike elastic body 7 may be used as the cutting means 18 without specific limitations. For example, it is possible to use a roller cutter which has a cutter roller with a cutting blade arranged at an outer circumferential face along a circumferential direction and an anvil roller for receiving the cutting blade, or the like. Alternatively, cutting may be performed with laser, heat or the like.

According to the stretchable sheet producing apparatus 11 of the present embodiment, following effects (a) to (c) are achieved owing to the proceeding portions 12a', 13a' of the upper belts 12a, 13a of the conveyance belts 12, 13 and the proceeding portions 12b', 13b' of the lower belts 12b, 13b of the conveyance belts 12, 13 which are inclined in the direction illustrated in FIG. 4, as described above.

(a) Attrition is less likely to occur at parts of the conveyance belt 12 and the conveyance belt 13 to contact to the threadlike elastic body 7. Therefore, slipping between the threadlike elastic body and the belt due to attrition of the belt is less likely to occur even after long term operation. Thus, stretchable sheets with the threadlike elastic body 7 accurately fixed in a desired state can be stably produced.

(b) The upper belts 12a, 13a and the lower belts 12b, 13b of the conveyance belts 12, 13 may be thicker and/or may be wider than widths Wa, Wb while suppressing the height T of the conveyance belts 12, 13 (that is, a distance T' between a part where the threadlike elastic body 7 is arranged between the upper side parts of the upper belts 12a, 13a and a part where the threadlike elastic body 7 is arranged between the lower side parts of the lower belts 12b, 13b; see FIG. 4).

With the above, durability of the conveyance belts 12, 13 can be improved without occurrence of trouble and the like for integrating the continuous-length sheets 50, 60 with the nip rollers 171, 172 and the like, so that la burden of maintenance and the like can be reduced. Further, contacting area between the threadlike elastic body and the conveyance belt is increased and slipping is less likely to occur between the belt and the threadlike elastic body, so that the stretchable sheet with the threadlike elastic body accurately fixed in a desired state can be stably produced.

The width Wa of the upper belts 12a, 13a and the width Wb of the lower belts 12b, 13b are preferably in a range of 25 to 75%, and more preferably in a range of 40 to 60% of the height T. The height T can be arbitrarily set, for example, in a range of 10 to 30 mm. In a case of producing the stretchable sheet used for a waist panel of a disposable diaper, the height T is preferably set in a range of 10 to 25 mm. Here, since relation between the width Wa and the width Wb and the height T depends on the setting of the inclination angles θ1, θ2 as well, there may be a case that the height T falls outside the above numerical range.

(c) Since two ridge portions are formed at the proceeding portions 12a', 12b', 13a', 13b' of the conveyance belts 12, 13, grip force for the threadlike elastic body is strengthened. More specifically, at the conveyance belts 12, 13, two ridge portions are formed by the proceeding portions 12a', 13a' of the upper belts 12a, 13a and two ridge portions are formed by the proceeding portions 12b', 13b' of the lower belts 12b, 13b. Therefore, slipping is further less likely to occur between the belts and the threadlike elastic body and the stretchable sheet with the threadlike elastic body accurately fixed in a desired state can be further stably produced.

Further, in the present embodiment, the returning portions 12a", 13a" of the upper belts 12a, 13a of the conveyance belts 12, 13 and the returning portions 12b", 13b" of the lower belts 12b, 13b of the conveyance belts 12, 13 are arranged approximately in parallel to each of the corresponding proceeding portions 12a', 13a', 12b', 13b', respectively, as illustrated in FIG. 4.

Therefore, the upper belts 12a, 13a and the lower belts 12b, 13b of the conveyance belts 12, 13 may adopt a belt having wide widths Wa, Wb respectively while further suppressing the height T of the conveyance belts 12, 13 (and the distance T' of the threadlike elastic body 7). Accordingly, it is possible to strengthen grip force for the threadlike elastic body 7 as well as to integrate the continuous-length sheets 50, 60 with the nip rollers 171, 172 and the like in a smooth manner.

Further, as illustrated in FIG. 4, the returning portions 12a", 13a" of the upper belts 12a, 13a and the returning portions 12b", 13b" of the lower belts 12b, 13b are separately arranged from the wound threadlike elastic body 7. Therefore, it is possible to prevent disarray of positional arrangement of the threadlike elastic body 7 and the like caused by the returning portion contacting to the threadlike elastic body 7.

In the producing apparatus 11 of the present invention, the upper belt 12a and the lower belt 12b of the conveyance belt 12 and the upper belt 13a and the lower belt 13b of the conveyance belt 13 are routed between the pair of pulleys having respective rotation axes inclined with respect to a straight line being perpendicular to the elastic body conveyance face S. The returning portions 12a", 13a", 12b", 13b" are arranged not in contact with the wound threadlike elastic body 7 without substantially twisting the upper belts 12a, 13a and the lower belts 12b, 13b.

The returning portions of the conveyance belts 12, 13 are preferred not to contact to the wound threadlike elastic body 7. As such a method, there has been a method to adopt a pulley to route around the belts with a conular belt contacting face or to arrange a guide to incline the returning portion to be oblique or to lay to be approximately horizontal. However, varying inclination with the pulley or the guide causes the belts to be twisted, so that attrition of the belt is likely to occur and life duration of the belt becomes relatively short owing to contacting to the pulley or guide for varying the angle.

On the other hand, in the present embodiment, since the returning portions are prevented from contacting without substantially twisting the belts, durability of the belts are improved and the stretchable sheet with the threadlike elastic body 7 accurately fixed in a desired state can be stably produced for a long term.

Further, the upper belt 12a of the conveyance belt 12 is provided with a belt supporting guide 190 which maintains the proceeding portion 12a' in an inclined state as illustrated in FIG. 4 between the pair of pulleys 121, 122, more specifically, between the rollers 123, as illustrated in FIG. 4. Although not illustrated in FIG. 2, the belt supporting guide 190 is a plate-shaped body with a predetermined width in the y-direction arranged from the position of P1 to the position of P2 in FIG. 2. That is, the belt supporting guide 190 is arranged from the upstream side of a position where the threadlike elastic body 7 contacts to the belt firstly to the downstream side of the nip rollers 171, 172. As illustrated in FIG. 4, the upper belt 13a of the conveyance belt 13 is also provided with a similar belt supporting guide 190.

Further, the lower belt 12b of the conveyance belt 12 is provided with a belt supporting guide 191 which maintains the proceeding portion 12b' in an inclined state as illustrated in FIG. 4 between the pair of pulleys 124, 125, more specifically, between the rollers 126, as illustrated in FIG. 4. Although not illustrated in FIG. 2, the belt supporting guide 191 is a plate-shaped body with a predetermined width in the y-direction arranged from the position of P1 to the position of P2 in FIG. 2. That is, the belt supporting guide 191 is arranged from the upstream side of a position where the threadlike elastic body 7 contacts to the belt firstly to the downstream side of the nip rollers 171, 172. As illustrated in FIG. 4, the lower belt 13b of the conveyance belt 13 is also provided with a similar belt supporting guide 191.

Here, the belt supporting guide 190 and the belt supporting guide 191 are held at a predetermined height by a supporting body (not illustrated) while maintaining a predetermined distance therebetween with a connecting portion 192.

According to the present embodiment, even when the wound threadlike elastic body 7 applies force to push the proceeding portions 12a', 13a' of the upper belts 12a, 13a' downward and force to push the proceeding portions 12b', 13b' of the lower belts 12b, 13b' upward, the inclined state and moving position thereof is stably maintained owing to the belt supporting guides 190, 191. Thus, disarray of positional arrangement of the threadlike elastic body 7, which is caused by, for example, fluctuation of distance between the proceeding portion of the upper belt and the proceeding portion of the lower belt, can be prevented.

Further, the belt supporting guides 190, 191 are arranged between the proceeding portion and the returning portion, so that contacting between the proceeding portion and the returning portion can be prevented.

Next, a method for producing a stretchable sheet using the abovementioned producing apparatus 11 will be described.

First, as illustrated in FIG. 3, the threadlike elastic body 7 is continuously unreeled and the unreeled threadlike elastic body 7 is introduced to the rotary arm 14 being the elastic body winding means in a stretched state.

More specifically, the threadlike elastic body 7 is continuously unreeled from the bobbin 70 having the threadlike elastic body 7 wound around using the reel-out roller 152. At the time of unreeling, the rotation speed of the reel-out roller 152 and braking of the tensor 151 are adjusted by the control unit (not illustrated) provided to the producing apparatus 11 based on the detection output of the tension of the threadlike elastic body 7 from the tension measuring unit 153. Then, the threadlike elastic body 7 is unreeled from the bobbin 70 with a predetermined tension.

Then, the threadlike elastic body 7 is introduced to the rotary arm 14. At the time of introducing, the threadlike elastic body 7 is introduced while adjusting the speed of the threadlike elastic body 7 introduced to the rotary arm 14 (elastic body winding means) to a constant speed with the feed roller 156 described above. The introducing speed is a speed corresponding to the winding speed to wind around the pair of conveyance belts 12, 13.

As illustrated in FIGS. 2 and 4, the threadlike elastic body 7 in a stretched state is continuously wound to the pair of conveyance belts 12, 13 using the rotary arm 14, and then, the continuously-wound threadlike elastic body 7 is conveyed between the pair of continuous-length sheets 50, 60 using the pair of conveyance belts 12, 13. More specifically, the threadlike elastic body 7 supplied into the rotary arm 14 in a stretched state is introduced into the arm portion 141 from the inlet port 145 and is led out from the outlet port 146 as passing through the shaft portion 142, the connecting portion 144, and the orbiting portion 143. The threadlike elastic body 7 to be led out from the outlet port 146 is led out while the rotary arm 14 is rotated, so that the threadlike elastic body 7 is wound to the outer periphery of the end part at the upstream side of the conveyance belt 12 (the upper belt 12a and the lower belt 12b) and the outer periphery side of the end part of the upstream side of the conveyance belt 13 (the upper belt 13a and the lower belt 13b). Here, owing to rotational driving of the conveyance belt 12 (the upper belt 12a and the lower belt 12b) and the conveyance belt 13 (the upper belt 13a and the lower belt 13b), the threadlike elastic body 7 is continuously wound like a spiral to the outer periphery side of the conveyance belt 12 (the upper belt 12a and the lower belt 12b) and the outer periphery side of the conveyance belt 13 (the upper belt 13a and the lower 13b). The continuously-wound threadlike elastic body 7 is conveyed between the pair of continuous-length sheets 50, 60 at the downstream side.

Here, the threadlike elastic body 7 wound to the pair of conveyance belts 12, 13 is stretched in a direction intersecting with the y-direction but not arranged in a direction perpendicular to the y-direction. To correct the wound threadlike elastic body 7 into the direction (x-direction) perpendicular to the y-direction, in a case that the threadlike elastic body 7 is wound as illustrated in FIG. 2, for example, the rotation speed of the upper belt 12a is set slower than the rotation speed of the lower belt 12b in the conveyance belt 12 and the rotation speed of the lower belt 13b is set slower than the rotation speed of the upper belt 13a in the conveyance belt 13. Accordingly, inclination of the threadlike elastic body 7 is gradually varied during conveyance in the y-direction and the inclination of the threadlike elastic body 7 can be corrected into the direction (x-direction) perpendicular to the y-direction by the time the threadlike elastic body 7 is conveyed between the pair of continuous-length sheets 50, 60.

As illustrated in FIG. 2, the continuous-length sheet 50 is previously folded at both sides in a longitudinal direction (both end parts in the x-direction) respectively to the outer face side by a folding means (not illustrated) or the like, and is supplied between the pair of nip rollers 171, 172 from the upper side of the conveyance belt 12 (the upper belt 12a and the lower belt 12b) and the conveyance belt 13 (the upper belt 13a and the lower belt 13b). Further, as illustrated in FIG. 2, the continuous-length sheet 60 is previously folded at the both sides in the longitudinal direction (both end parts in the x-direction) respectively to the outer face side by a folding means (not illustrated) or the like, and is supplied between the pair of nip rollers 171, 172 from the lower side of the conveyance belt 12 (the upper belt 12a and the lower belt 12b) and the conveyance belt 13 (the upper belt 13a and the lower belt 13b). Here, adhesive is applied to the inner face side of the continuous-length sheet 50 and/or the continuous-length sheet 60 before the sheets are supplied between the pair of nip rollers 171, 172. The adhesive may be applied to the entire face in a pattern of spirals, or may be applied in a solid manner.

Subsequently, the threadlike elastic body 7 is fixed between the pair of continuous-length sheets 50, 60 in a stretched state using the nip rollers 171, 172. More specifically, a continuous member having the continuously-wound threadlike elastic body 7 arranged between the pair of continuous-length sheets 50, 60 is supplied between the pair of nip rollers 171, 172, and the threadlike elastic body 7 is fixed between the pair of continuous-length sheets 50, 60 in a stretched state.

Subsequently, the threadlike elastic body 7 extended from both end parts in the width direction (x-direction) of the pair of continuous-length sheets 50, 60 is cut by the abovementioned cutter 180.

Subsequently, as illustrated in FIG. 5, the folding at both the end parts in the x-direction of the continuous-length sheets 50, 60 folded to the outer face side are corrected respectively by a folding means (not illustrated) or the like. Thus, it is possible to continuously produce a continuous-length stretchable sheet 3A in which the threadlike elastic body 7 is fixed between the pair of continuous-length sheets 50, 60 in a state of being stretched in the direction intersecting with the y-direction. The produced continuous-length stretchable sheet is discontinuously cut along the x-direction with known cutting means (not illustrated). The interval of the discontinuous cutting is the same as a dimension of the waist panel 3 provided to the diaper 1. With the above, it is possible to continuously produce the waist panels 3 (stretchable sheets).

As a method of producing the diaper 1 which includes the waist panels 3, a continuous member of the absorbent body 2 is produced in a separate process with a known method. The continuous member of the absorbent body 2 includes a continuous member of the topsheet 21, a continuous member of the backsheet 22, a plurality of the absorbent members 23, 23, . . . arranged discontinuously in the conveyance direction (y-direction) between the continuous members of both the sheets 21, 22, a plurality of the elastic members 25 and continuous members of the standing gather forming sheets 24 arranged as being elongated at both side parts in the conveyance direction (y-direction) of the continuous member of the topsheet 21.

A pair of the waist panels 3 is arranged for each absorbent member 33 included in the continuous member of the absorbent body 2 as being protruded bilaterally outward in the x-direction while the continuous member of the absorbent body 2 produced as described above is conveyed in the conveyance direction (y-direction). Thus, a continuous member of the diaper 1 is produced. Here, the conveyance direction (y-direction) of the continuous member of the absorbent body 2 is the same as the conveyance direction (y-direction) when producing the waist panel 3 (stretchable sheet). Therefore, it is not required to rotate the waist panel 3 (stretchable sheet) by 90°. Subsequently, the continuous member is cut into dimensions of each diaper 1 with known cutting means (not illustrated). Thus, the diaper 1 can be produced.

Not being limited to the abovementioned embodiments in any way, the method for producing a stretchable sheet and the method for producing a disposable diaper of the present invention may be appropriately modified.

For example, although the conveyance belt 12 and the conveyance belt 13 are symmetric in the embodiment, a dissymmetric structure is adaptable as well. For example, the inclination angle θ1 of the proceeding portion of the upper belt and/or the inclination angle θ2 of the proceeding portion of the lower belt may be set to a different value between the conveyance belt 12 and the conveyance belt 13. That is, each value of θ1 and θ2 may be freely paired between the conveyance belt 12 and the conveyance belt 13.

Further, means disclosed in Patent Literature 1 or JP 2010-22588 A may be adopted as elastic body winding means.

Further, instead of introducing continuous-length sheets narrowed by folding back both end parts in the width direction respectively to the outer face side between the pair of nip rollers 170, 171 and fixing the threadlike elastic body between the continuous-length sheets, it is also possible to introduce continuous-length sheets without both end parts in the width direction folded back and to fix the threadlike elastic body between the continuous-length sheets. Further, in a case of folding, folding may be performed only on the end part in the width direction of the sheet at one side or only on the end part of one continuous-length sheet. Further, the threadlike elastic body 7 may not have the inclination corrected to the direction (x-direction) perpendicular to the y-direction or may be fixed to the pair of continuous-length sheets 50, 60 as remaining at angles wound to the conveyance belt 12 without being corrected.

The up-down direction herein conveniently denotes a direction approximately perpendicular to the elastic body conveyance face S. That is, the pair of conveyance belts in the present invention is not limited to arrangement of being in parallel to the horizontal direction of the elastic body conveyance face S. For example, the elastic body conveyance face S may be arranged in parallel to the vertical direction or may be arranged to as being angled with respect to the horizontal face by 45°. In a case that the elastic body conveyance face S is arranged to be in parallel to the horizontal direction, the abovementioned upper belt and lower belt are arranged in a two-tier fashion in the horizontal direction, not in a two-tier fashion in the up-down direction.

Further, the stretchable sheet produced with the producing method of the present invention can be used for not only the waist panel 3 of the disposable diaper 1 but also a waist portion of a disposable diaper, a waist portion of a pant-type disposable diaper, a pant-type sanitary napkin, disposable underwear, an ear-hook portion of a disposable mask, a sheet for cleaning, a bandage and the like.

In relation to the abovementioned embodiments, the present invention further discloses the following producing apparatus and absorbent article producing methods.

[1] An apparatus for producing a stretchable sheet, comprising:
a pair of conveyance belts which is separately arranged;
elastic body winding means which winds a threadlike elastic body around the pair of conveyance belts and orients the threadlike elastic body in a direction intersecting with a conveyance direction of continuous-length sheets; and
integrating means which fixes the threadlike elastic body to the continuous-length sheets,
wherein the pair of conveyance belts includes an upper belt and a lower belt respectively,
each of the upper belt and the lower belt is an endless rotating belt including a proceeding portion which conveys the threadlike elastic body while contacting to the wound threadlike elastic body and a returning portion which moves in a direction opposite to the proceeding portion,
the proceeding portion of the upper belt is inclined so that an upper side is located closer than a lower side to a center position between the conveyance belts, and
the proceeding portion of the lower belt is inclined so that a lower side is located closer than an upper side to the center position between the conveyance belts.

[2] The apparatus according to subject [1], wherein the returning portion is arranged approximately in parallel to the proceeding portion respectively at the upper belt and the lower belt.

[3] The apparatus according to subject [1] or subject [2], wherein each of the upper belt and the lower belt is routed between a pair of pulleys having respective rotation axes inclined with respect to a direction being perpendicular to a conveyance face of the threadlike elastic body, and the returning portion is arranged not in contact with the threadlike elastic body wound around the pair of conveyance belts without substantially twisting the upper belt and the lower belt.

[4] The apparatus according to any one of subjects [1] to [3], wherein each of the upper belt and the lower belt is routed between the pair of pulleys, and a belt supporting guide which maintains the proceeding portion in the inclined state is arranged between the pair of pulleys.

[5] The apparatus according to any one of subjects [1] to [4], wherein a distance between the proceeding portion and the returning portion at each of the upper belt and the lower belt of the conveyance belts is in a range of 3 to 25%, and preferably 5 to 15%, of height of the conveyance belts.

[6] The apparatus according to any one of subjects [1] to [5], wherein the integrating means includes nip rollers, and a value of the height of the conveyance belts is equal to or less than 25%, and preferably 20%, of a diameter of the nip roller.

[7] The apparatus according to any one of subjects [1] to [6], wherein each of inclination angles ($\theta 1$, $\theta 2$) of the proceeding portions of the upper belt and the lower belt with respect to the elastic body conveyance face is in a range of 1 to 45°, preferably 5 to 20°.

[8] The apparatus according to any one of subjects [1] to [7], wherein a width of the upper belt and a width of the lower belt of the conveyance belts are in a range of 25 to 75%, preferably 40 to 60%, of the height of the conveyance belts.

[9] The apparatus according to any one of subjects [1] to [8], wherein two ridge portions are formed by the proceeding portion of the upper belt and two ridge portions are formed by the proceeding portion of the lower belt at the conveyance belts.

[10] A method for producing a stretchable sheet which produces a stretchable sheet using the apparatus according to any one of subjects [1] to [9].

[11] A method for producing a disposable diaper which includes an absorbent body and right-left waist panels continuously arranged to both of right-left sides of the absorbent body in a longitudinal direction, the method comprising producing a stretchable sheet with the apparatus according to any one of subjects [1] to [9], and producing the disposable diaper using the stretchable sheet as a forming material of the waist panels.

INDUSTRIAL APPLICABILITY

According to the apparatus for producing a stretchable sheet of the present invention, slipping is less likely to occur between the belt and the threadlike elastic body even when operated for a long term, and a stretch sheet with the threadlike elastic body accurately fixed in a desired state can be stably produced.

The invention claimed is:
1. An apparatus for producing a stretchable sheet, comprising:
two sets of conveyance belts which are separately arranged;
elastic body winding means which winds a threadlike elastic body around the two sets of conveyance belts and orients the threadlike elastic body in a direction intersecting with a conveyance direction of a pair of continuous-length sheets; and
integrating means which fixes the threadlike elastic body to the continuous-length sheets,
wherein each set of the conveyance belts includes an upper belt and a lower belt respectively,
each of the upper belt and the lower belt is an endless rotating belt including a proceeding portion which conveys the threadlike elastic body while contacting to the wound threadlike elastic body and a returning portion which moves in a direction opposite to the proceeding portion, the proceeding portion of the upper belt is inclined so that an upper edge is located closer than a lower edge to a center position between the two sets of the conveyance belts, and the proceeding portion of the lower belt is inclined so that a lower edge is located closer than an upper edge to the center position between the two sets of the conveyance belts.

2. The apparatus according to claim 1, wherein the returning portion is arranged approximately in parallel to the proceeding portion respectively at the upper belt and the lower belt.

3. The apparatus according to claim 1,
wherein each of the upper belts and the lower belts of the two sets of conveyance belts is routed between a pair of pulleys having respective rotation axes inclined with respect to a direction being perpendicular to a conveyance face of the threadlike elastic body, and each of the returning portions of the upper belts and the lower belts of the two sets of conveyance belts is arranged not in contact with the threadlike elastic body wound around the two sets of conveyance belts without substantially twisting the upper belts and the lower belts.

4. The apparatus according to claim 1,
wherein each of the upper belts and the lower belts of the two sets of conveyance belts is routed between the pair of pulleys, and a belt supporting guide which maintains each of the proceeding portions in the inclined state is arranged between the pair of pulleys.

5. The apparatus according to claim 1, wherein a distance between the proceeding portion and the returning portion at each of the upper belt and the lower belt of the conveyance belts is in a range of 3% to 25% of height of the conveyance belts, wherein the height of the conveyance belts is a distance between the upper edge of the proceeding portion of the upper belt and the lower edge of the proceeding portion of the lower belt in a direction perpendicular to an elastic body conveyance face of the threadlike elastic body.

6. The apparatus according to claim 1,
wherein the integrating means includes nip rollers, and
a value of height of the conveyance belts is equal to or less than 25% of a diameter of the nip roller, wherein the height of the conveyance belts is a distance between the upper edge of the proceeding portion of the upper belt and the lower edge of the proceeding portion of the lower belt in a direction perpendicular to an elastic body conveyance face of the threadlike elastic body.

7. The apparatus according to claim 1, wherein each of inclination angles (θ1, θ2) of the proceeding portions of the upper belt and the lower belt with respect to the elastic body conveyance face is in a range of 1 to 45°.

8. The apparatus according to claim 1, wherein width of the upper belt and width of the lower belt of the conveyance belts are in a range of 25 to 75% of height of the conveyance belts, wherein the height of the conveyance belts is a distance between the upper edge of the proceeding portion of the upper belt and the lower edge of the proceeding portion of the lower belt in a direction perpendicular to an elastic body conveyance face of the threadlike elastic body.

9. The apparatus according to claim 1, wherein the upper belts are inclined so that two ridge portions are formed by the proceeding portions of the upper belts, and the lower belts are inclined so that two ridge portions are formed by the proceeding portions of the lower belts of the conveyance belts.

10. A method for producing a stretchable sheet which produces a stretchable sheet using the apparatus according to claim 1, the method comprising:
unreeling the threadlike elastic body continuously, and then, introducing the unreeled threadlike elastic body to the elastic body winding means in a stretch state;

winding the threadlike elastic body in a stretch state around the two sets of conveyance belts using the elastic body winding means, and then, conveying the continuously-wound threadlike elastic body between the pair of continuous-length sheets using the two sets of conveyance belts; and fixing the threadlike elastic body between the pair of continuous-length sheets in a stretch state using the integrating means.

11. A method for producing a disposable diaper which includes an absorbent body and right-left waist panels continuously arranged to both of right-left sides of the absorbent body in a longitudinal direction, the method comprising:

producing the disposable diaper using a stretchable sheet as a forming material of the waist panels, producing a continuous member of the absorbent body including a continuous member of a topsheet, a continuous member of a backsheet, a plurality of the absorbent members arranged discontinuously in a conveyance direction between the continuous members of both of the topsheet and backsheet, producing a continuous member of the diaper by arranging a pair of stretchable sheets for each absorbent member included in the continuous member of the absorbent body as being protruded bilaterally outward in a direction perpendicular to the conveyance direction while conveying the continuous member of the absorbent body in the conveyance direction, and producing the disposable diaper by cutting the continuous member of the diaper into dimensions of each diaper.

* * * * *